United States Patent [19]

Ng et al.

[11] 4,080,310

[45] Mar. 21, 1978

[54] AMPHOTERIC CONDITIONING SHAMPOO

[75] Inventors: Louis Ng; George Guttler, both of Clifton, N.J.

[73] Assignee: Beecham Group Limited, England

[21] Appl. No.: 695,096

[22] Filed: Jun. 11, 1976

[30] Foreign Application Priority Data

Jun. 12, 1975 United Kingdom ............... 25136/75

[51] Int. Cl.² .......................... C11D 1/38; C11D 1/58
[52] U.S. Cl. ..................... 252/544; 252/547; 252/548; 252/DIG. 7; 252/DIG. 13; 424/70
[58] Field of Search ............... 252/544, 546, 547, 548, 252/DIG. 1, DIG. 13, DIG. 7; 424/70, 71, 47, DIG. 1, DIG. 2

[56] References Cited

U.S. PATENT DOCUMENTS

| 3,917,817 | 11/1975 | Vanlerberghe et al. ..... 252/DIG. 13 |
| 3,964,500 | 6/1976 | Drakoff ....................... 252/DIG. 13 |
| 3,980,769 | 9/1976 | Ghilardi et al. ............. 252/DIG. 13 |
| 4,001,394 | 1/1977 | Fogel et al. ................. 252/DIG. 13 |
| 4,009,256 | 2/1977 | Nowak et al. ............... 252/DIG. 13 |

*Primary Examiner*—Thomas J. Herbert, Jr.
*Attorney, Agent, or Firm*—Jacobs & Jacobs

[57] ABSTRACT

Shampoo compositions containing hair cleansing and conditioning components and characterized by 5 to 50% w/w of amphoteric detergent as sole ionic detergent and 0.5 to 3.0% w/w of cationic or quaternary resin, the pH being from 3 to 9, preferably 4 to 7. The amphoteric detergent may be, for example, an N-alkyl-β-aminopropionate or N-alkyl-β-iminodipropionate. Suitable resins are cationic polyamide polymers or a cationic starch or cellulose derivatives.

3 Claims, No Drawings

AMPHOTERIC CONDITIONING SHAMPOO

This invention relates to shampoo compositions with hair cleansing and conditioning components.

According to a widely accepted definition, a shampoo is a suitable detergent for washing the hair which should also leave the hair in good condition. The first requirement is easily met with a wide variety of available detergents, but the second requirement is not so easily satisfied. The difficulty arises because in cleansing the hair of dirt, detergents remove a considerable amount of the natural oils normally present on the hair. These oils contribute substantially to the manageability of the hair, and their removal leaves the hair very dry, fluffy and difficult to arrange into the desired style. To overcome this problem conditioning agents have been included in many shampoo compositions. Examples of such conditioning agents are hydrolyzed protein, lanolin alcohols, other fatty alcohols, esters and amides, as well as polyvinylpyrrolidone.

Amphoteric detergents are said to have a more gentle action than other classes of detergents, and consequently are used in baby shampoos and as secondary detergents in adult shampoos where their presence is said to improve the conditioning properties of the shampoo.

This invention is based on the discovery that a shampoo with good cleansing and conditioning properties results when the composition includes an amphoteric detergent as the sole detergent component, and a cationic or quaternary resin.

Accordingly, the present invention provides an aqueous shampoo composition comprising 5 to 50% w/w of amphoteric detergent as the sole ionic detergent component, and from 0.5 to 3.0% w/w of cationic or quaternary resin, the pH of the composition being from 3 to 9.

Suitable amphoteric detergents include N-alkyl-$\beta$-aminopropionates [RNHCH$_2$CH$_2$COOM] or N-alkyl-$\beta$-iminodipropionates [RN(CH$_2$CH$_2$COOM)$_2$] where R is an alkyl group of 8 to 18 carbon atoms and M is hydrogen or a salt forming cation; betaines such as alkylbetaines [R(CH$_3$)$_2$N$^+$CH$_2$COO$^-$], amido-betaines [RCON$^+$(CH$_3$)$_2$CH$_2$COO$^-$] or sulphobetaines [RCON(CH$_3$)$_2$(CH$_2$)$_3$SO$_3^-$] wherein R is an alkyl radical of from 8 to 18 carbon atoms; N-acyl sarcosinates [RCONCH$_3$COOM] where R is an alkyl radical of from 8 to 18 carbon atoms and M is hydrogen or a salt forming ion; substituted imidazolines

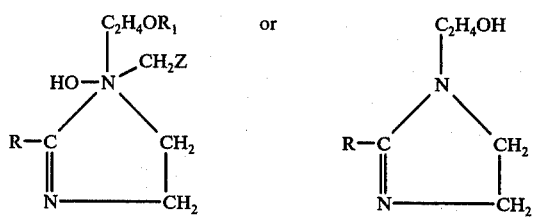

wherein R is an alkyl radical of from 8 to 18 carbon atoms, R$_1$ is hydrogen, a salt forming ion or CH$_2$COOM wherein M is hydrogen or a salt forming ion, and Z is COOM or CH$_2$COOM wherein M is hydrogen or a salt forming ion.

Suitable resins include cationic polyamide polymers typified by a low molecular weight adipic acid/diethylenetriamine polyamide of formula

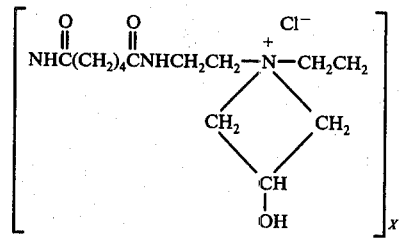

wherein X is about 40 to 60 (Delsette 101 ex Hercules Inc., U.S.A.); copolymers of vinylpyrrolidone and dimethylaminoethylmethacrylate quaternised with diethyl sulphate (Gafquat 755 ex GAF Corporation, U.S.A.); cationic starch and cellulose derivatives, e.g. Cato starch ex National Starch and Chemical Corporation, U.S.A. and Polymer JR ex Union Carbide (c.f. U.S. Pat. No. 3,472,840).

The preferred pH of the composition is in the range 4 to 7.

In addition to the amphoteric detergent and cationic or quaternary resin, the shampoos of this invention may include conventional additives such as protein hydrolysates for additional conditioning properties, quaternary ammonium monomers to improve manageability and reduce fly-away, silicone derivatives to aid wet and dry compatibility, alkanolamides and amine oxides to modify foam properties, plasticisers such as alcohols and glycols to modify the surface properties of the resin (e.g. to improve flexibility or reduce stickiness), perfumes, colouring, preservatives and thickening agents.

The shampoos may be formulated as clear or opaque liquids, gels or lotions.

The following Examples illustrate the invention:

| | % by weight |
|---|---|
| Example 1 | |
| N-Lauryl, myristyl-$\beta$-amino propionic acid | 25.0 |
| Cationic polyamide resin (Delsette 101 ex Hercules Inc.) | 3.0 |
| Ethoxylated coconut monoethanolamide (Amidox C5 ex Stepan Chemical Co.) | 4.0 |
| Perfume, colour, preservative | Q.S. |
| Water | to 100.00 |
| Example 2 | |
| Coco-imidazoline dicarboxylic acid derivative, sodium salt (Miranol C2M ex Miranol Chemical Co.) | 20.0 |
| Cationic polyamide resin (Delsette 101, ex Hercules Inc.) | 0.5 |
| Lauric diethanolamide | 4.0 |
| Silicone glycol | 0.2 |
| Perfume, colour, preservative | Q.S. |
| Water | to 100.0 |
| Example 3 | |
| N-Lauryl, myristyl-$\beta$-amino propionic acid, triethanolamine salt | 10.0 |
| Cationic polyamide resin (Delsette 101, ex Hercules Inc.) | 3.0 |
| Ethylene diamine tetraacetic acid | 0.5 |
| Lauryl dimethylamine oxide | 2.0 |
| Perfume, colour, preservative | Q.S. |
| Water | to 100.0 |
| Example 4 | |
| Coco-imidazoline dicarboxylic acid derivative, sodium salt (Miranol C2M ex Miranol Chemical Co.) | 12.0 |
| Quaternized vinyl pyrrolidone resin (Gafquat 755, ex GAF Corp.) | 1.5 |
| Collagen hydrolysate (Wilson's protein WSP-X250) | 2.0 |
| Lauric monoethanolamide | 2.0 |
| Perfume, colour, preservative | Q.S. |
| Water | to 100.0 |
| Example 5 | |
| N-Lauryl $\beta$-iminodipropionic acid, | |

| | % by weight |
|---|---|
| disodium salt | 15.0 |
| Cationic cellulose resin (Polymer JR ex Union Carbide) | 2.0 |
| N-(Stearoyl colamino formyl methyl) pyridinium chloride | 2.0 |
| Collagen hydrolysate | 2.0 |
| Ethylene diamine tetraacetic acid, disodium salt | 0.2 |
| Ethoxylated lauric monoethanolamide | 3.0 |
| Silicone glycol | 1.0 |
| Perfume, colour, preservative | Q.S. |
| Water | to 100.0 |
| *Example 6* | |
| Quaternized vinyl pyrrolidone resin | 1.5 |
| N-Lauryl, myristyl-β-amino propionic acid, sodium salt | 10.0 |
| Coconut betaine | 2.0 |
| Perfume, colour, preservative | Q.S. |
| Water | to 100.0 |
| *Example 7* | |
| Quaternized vinyl pyrrolidone resin | 1.35 |
| N-Lauryl, myristyl-β-amino propionic acid, sodium salt | 5.50 |
| N-Lauryl sarcosinate (sodium salt) | 3.90 |
| Perfume, colour, preservative | Q.S. |
| Water | to 100.00 |

The above seven shampoos were evaluated on female and male models. It was found that the products gave good shampooing properties and, on drying the hair, they provided excellent conditioning, styling and holding characteristics.

What we claim is:

1. An aqueous shampoo composition comprising, as the sole ionic detergent component, 5 to 50% w/w of an amphoteric detergent selected from the group consisting of an N-alkyl-β-aminopropionate and N-alkyl-β-iminodipropionate wherein alkyl has 8 to 18 carbon atoms and from 0.5 to 3.0% w/w of a cationic resin having the formula:

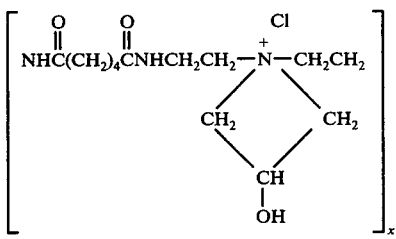

wherein X is about 40–60, the pH of the composition being from 3 to 9.

2. A composition as claimed in claim 1 having a pH in the range 4 to 7.

3. A composition as claimed in claim 1, further comprising a protein hydrolysate conditioner and a modifier of the surface properties of the resin.

* * * * *